United States Patent [19]

Naujokas

[11] Patent Number: 5,712,410
[45] Date of Patent: Jan. 27, 1998

[54] GAS PHASE CRYSTALLIZATION OF DIMETHYL TEREPHTHALATE

[75] Inventor: Andrius A. Naujokas, Webster, N.Y.

[73] Assignee: Eastman Kodak Company, Rochester, N.Y.

[21] Appl. No.: 811,085

[22] Filed: Mar. 3, 1997

[51] Int. Cl.$^6$ .................................................. C07C 67/60
[52] U.S. Cl. ........................... 560/78; 528/481; 528/496; 568/854
[58] Field of Search ........................... 560/78; 521/48.5; 528/481, 496; 568/854

[56] References Cited

U.S. PATENT DOCUMENTS

| | | |
|---|---|---|
| 3,257,335 | 6/1966 | Whitfield, Jr. et al. . |
| 3,907,868 | 9/1975 | Currie et al. . |
| 4,163,860 | 8/1979 | Delattre et al. . |
| 5,051,528 | 9/1991 | Naujokas et al. . |
| 5,298,530 | 3/1994 | Gamble et al. . |
| 5,414,022 | 5/1995 | Toot, Jr. et al. . |
| 5,432,203 | 7/1995 | DeBruin et al. ..................... 521/48.5 |
| 5,576,456 | 11/1996 | Gamble et al. ..................... 560/78 |

*Primary Examiner*—Samuel Barts
*Attorney, Agent, or Firm*—Arthur H. Rosenstein

[57] ABSTRACT

There is described a process for depolymerizing polyethylene naphthalate polyester to monomer components which then can be used to make virgin polyester.

6 Claims, 1 Drawing Sheet

GAS PHASE CRYSTALLIZATION OF DIMETHYL TEREPHTHALATE

FIELD OF THE INVENTION

This invention relates to a process for recovering ester and glycol components from polyethylene terephthalate.

BACKGROUND OF THE INVENTION

Polyethylene terephthalate, which is abbreviated as PET, has outstanding physical properties for a number of uses, such as in textile, film and other applications. It has been found to be particularly useful as a film base for photographic materials and the photographic industry has used it as a film support in new photographic products. PET, as well as its precursor dimethyl terephthalate abbreviated as DMT, is quite costly. The polymer is a linear polyester produced from ethylene glycol and DMT conventional polymerization processes. Due to relatively high cost of the polyester and to minimize the need for disposal it is desirable to recycle and reuse waste PET.

Two distinctly different routes have been used to recycle polyesters in general. The first route is direct recycle. This can be done when the polyester scrap is completely clean or can be cleaned by washing or other means. The clean(ed) polyester is used in place of virgin polyester at the appropriate point in the manufacturing process. Depending upon the manufacturing steps in the process, degradation of the polyester can occur during such steps as melting and extrusion due to thermal and shear effects. This results in a deterioration of the physical properties of the polyester, such as a lowering of molecular weight. Generally for high grade products, such as film base, recycle polyester is blended in limited amounts with virgin polyester. Since PET have relatively high melting and softening temperatures significant degradation of the polyester can be expected. Furthermore, if the polyester scrap is contaminated, or is not thoroughly cleaned, additional degradation of properties can occur.

The second route is depolymerization of the polyester to component monomers, recovering the monomers and then using them to produce new polyester. This route has been used for recovery of monomers from polyethylene terephthalate polyester. Recovery techniques are described, for example in U.S. Pat. Nos. 5,414,022; 4,163,860; 3,907,868; and 3,257,335.

In polyester scrap recovery, selected reaction by-products are added to the reactor in order to decrease the molecular weight of the polyester by depolymerization to monomer components. The diester form of recovered monomer is preferred, since the diester is more volatile than the acid and is more readily purified.

The generic polyester reaction can be written as two steps:
Step 1: Transesterification
 Dimethyl Ester+Glycol=Half Ester+Monomer+Methanol

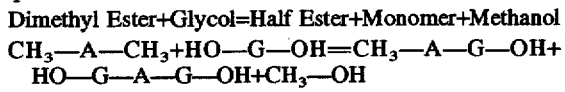

Step 2: Polycondensation
 Monomer=Polymer+Glycol

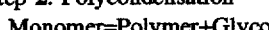
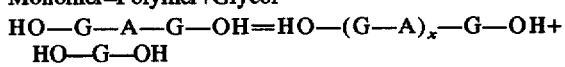

wherein:
 A is a difunctional acid moiety (—COO—T—COO—)
 T is benzene for terephthalate
 G is an alkylene moiety (—CH$_2$—CH$_2$—for ethylene glycol)
 x is the number of repeat units in an average molecular chain, i.e., the degree of polymerization.

In the transesterification step the difunctional acid can be substituted for the diester and the reaction product will be water. Likewise other alcohols may be substituted for methanol to form the diester.

In polyester scrap recovery the above reactions are driven in the reverse direction, under appropriate reaction conditions and in the presence of catalysts, by addition of excess amounts of alcohol, glycol or both. Reacting the polymer with excess glycol will reverse the polycondensation reaction and will produce monomer (one diacid moiety with two glycols attached.) Other oligomers will be also present, as determined by the equilibrium conditions for the particular reaction. Reacting alcohol with monomer will then produce the difunctional ester product. Similar results will be obtained when excess alcohol (such as methanol) is reacted with the polymer. The final composition will again be governed by equilibrium. All the major components shown in the transesterification reaction, and a distribution of higher oligomers, are the reaction products.

A low pressure methanolysis process for recovery of components from scrap polyethylene terephthalate is disclosed in U.S. Pat. Nos. 5,051,528; 5,298,530; 5,414,022; 5,432,203 and others. The reactor product consists of a gas phase stream containing mainly of dimethyl terephthalate (DMT), ethylene glycol (EG), methanol and small amounts of impurities. The amount of impurities in the reactor product stream depends on the votality with respect to DMT. If the volatility is low enough some of the contaminants will be carried out of the reactor in sufficient concentrations. Typically this stream is cooled and conditioned to produced a liquid with DMT dissolved in methanol. The temperature of this stream is then reduced and some of the methanol removed causing the dissolved DMT to precipitate as crystals. The solids are then separated by an appropriate separation method such as filtration. The crystals are then washed to remove most of the EG and other contaminants. The crude DMT is then distilled to obtain polymer grade material. As can be seen, the product stream from the reactor is processed using a number of steps that involve solutions as well as two phase streams. Two phase streams are generally difficult to handle. The slurry tends to settle, bridge and provides unreliable transport properties. Crystallization is critical since it constitutes a purification step and the crystal size and size distribution influences the filtration and washing of the crude DMT.

SUMMARY OF THE INVENTION

The present invention provides a process for depolymerizing scrap polyethylene terephthalate polyester to monomer components by a low pressure methanolysis process followed by gas phase crystallization to monomer components that then can be used to make additional polyester.

A method has been discovered that eliminates the liquid phase crystallization step as well as some other processing steps. It was found that under appropriate conditions of temperature and composition DMT can be crystallized directly from the gas phase reactor product stream without condensing other reaction streams, such as methanol and EG. This is accomplished by adjusting the temperatures by heat exchange and the composition and also the temperature through addition of an inert gas such as nitrogen to the reactor product stream. The resulting DMT crystals are collected in a receiving vessel while the methanol and a portion of EG leave the crystallizer as gas. The EG and methanol are then condensed by cooling in a separate condenser. The dry DMT crystals are then removed from the crystallizers by appropriate means. The crystallization step can be staged to facilitate the recovery of DMT and to minimize the condensation of EG on the crystal surface. This invention is an improvement of the Low Pressure methanolysis process.

This process, and variations thereof, provide advantageous means for recovering monomer components from PET polyester. The benefits and advantages of the process will be apparent from the detailed discussion of the process below.

Figure 1:
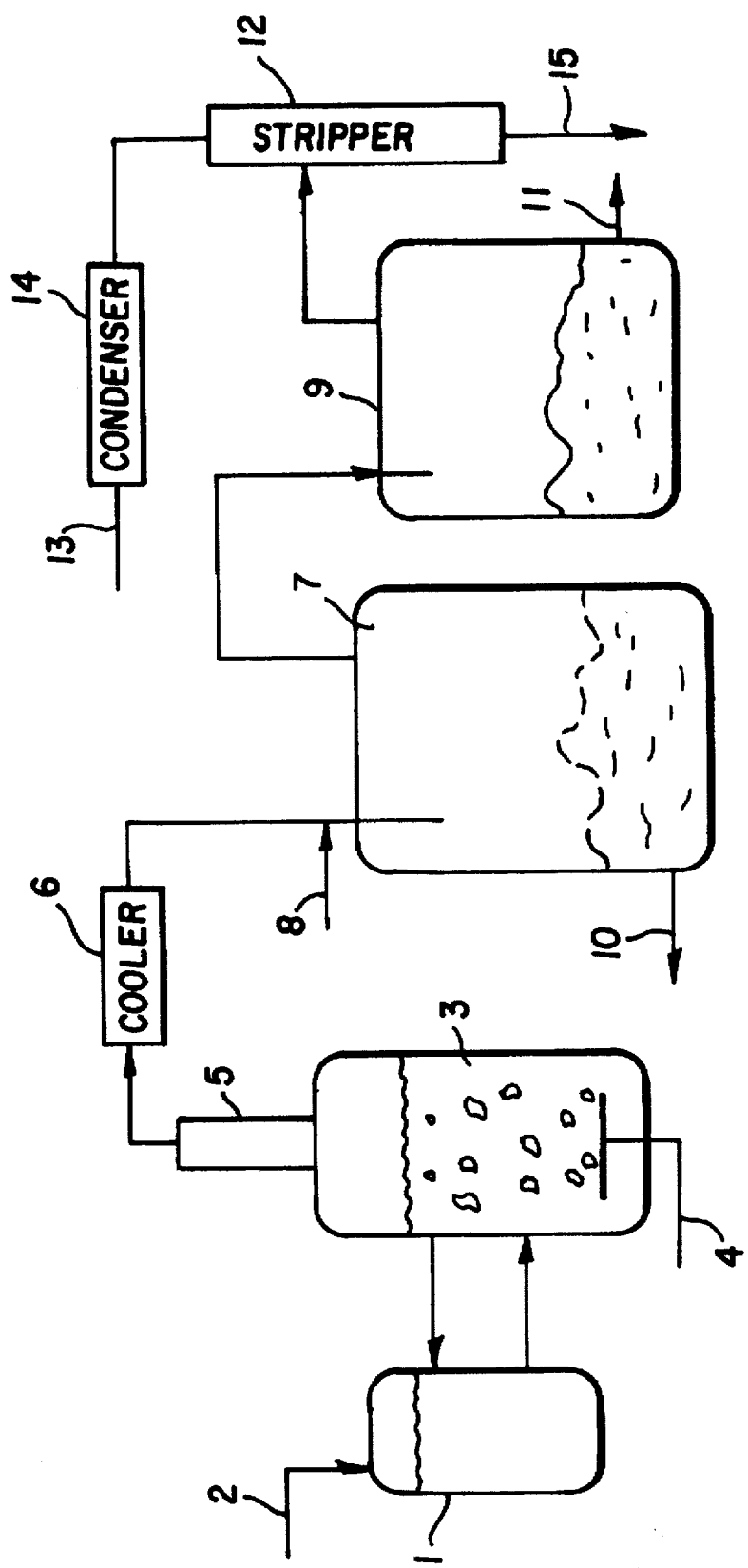
FIG. 1 is a schematic of a low pressure methanolysis PET scrap recovery plant.

For a better understanding of the present invention, together with other and further objects, advantages and capabilities thereof, reference is made to the following detailed description and appended claims in connection with the preceding drawings and description of some aspects of the invention.

DETAILED DESCRIPTION OF THE PREFERRED EMBODIMENTS

In the present invention low pressure methanolysis (pressure of ambient to 50 psi) is used to depolymerize the polyester scrap. The crude product stream consisting of DMT, EG and containing some impurities is produced by passing a superheated stream (temperatures of 230° C. to 290° C.) of alcohol such as methanol vapor through a reactor containing a melt of relatively low molecular weight distribution of oligomers of PET (Mw of 1000 to 3000). The methanol provides the reactant to react the oligomers to the final products of DMT and EG. In addition the methanol vapor also acts as a stripping agent to drive the DMT and EG out of the reactor. This stream is then processed according to the invention to product crystalline DMT and to separate the other components from the solid.

The advantages of the present invention are that slurry formation and handling and liquid phase crystallizers are eliminated, large DMT crystals are formed, DMT loss due to solubility in methanol is eliminated, higher DMT purity is obtained, methanol and EG can be readily separated using vapor feed stripper, DMT carryover with EG is minimized or eliminated and it is possible to eliminate crystal washing.

FIG. 1 shows the gas phase crystallization process in a low pressure methanolysis plant. Scrap polyester 2 is dissolved in reactor 1 and transferred to reactor 3. Methanol 4 or some other alcohol vapor is sparged into reactor 3 to supply the reactant and stripping medium to produce the DMT and EG product stream. To reduce the molecular weight if the polyester polymer feed part of the melt from reactor 3 is recycled to reactor 1. Both reactors 1 and 3 can be operated at temperatures of 230° C. to 290° C. and pressured from ambient to 50 psi or higher.

The resulting monomers are sent through rectifier 5 to a cooling chamber 6 and then to a crystallizer 7 to which an inert gas such as nitrogen, $CO_2$, helium or the like 8 is added. The gas phase crystallizer is at a temperature of 20° C. to 140° C. and, if desired, a second crystallizer 9 can be used. DMT 10 is removed from crystallizer 7 and more DMT 11 can be removed from crystallizer 9. The ethylene glycol and methanol vapor stream is sent into stripper 12 where methanol 13 is the overhead product and is removed by condenser 14 and ethylene glycol 15 is obtained as stripper 12 (bottoms stream).

The embodiments of the invention are illustrated in the following example.

EXAMPLE 1

The Experimental work was carried out using a laboratory size reactor system. The lab reactor used in the experiments consisted of a 11 cm diameter, 30 cm high stainless steel vessel fitted with a three neck ground joint stainless steel cover. The reactor was heated using a molten salt bath. The reaction methanol was preheated by passing liquid methanol through a coil immersed in a salt bath and then injected at the bottom of the reactor. The vapor phase products consisting of methanol DMT, EG and some minor contaminants were passed through a heated glass line to a 4 liter capacity glass receiver. Before the product stream entered the receiver nitrogen gas was introduced to cool and dilute the stream in such a way that the dew points of methanol and EG were below the temperature of the process stream. To capture residual DMT a second 4 liter receiver flask was connected in series with the first receiver.

The reactor was operated at 270° C. with a 6 ml/min methanol flow rate and 14 cm depth of reactor melt. The apparatus was under atmospheric pressure. The scrap was fed into the reactor periodically to maintain the melt depth at constant value. A room temperature nitrogen stream at 0.6 scfm was added to the reactor product stream before it entered the first receiver. This reduced the temperature of the stream to 83° C. Solid crystals formed in the first and second receivers. The bulk of the crystals were found in the first receiver. The crystals were large (up to one inch in length and up to ⅛ inch in width).

FIG. 1 shows one embodiment of the invention in a Low Pressure methanolysis PET scrap recovery plant. The schematic representation shows two gas phase DMT crystallizers. More stages can be used if there is an advantage in separating unwanted components from DMT. The optimal design will depend on the composition of contaminants. The DMT can be continuously or periodically removed from the crystallizers. The crude DMT then can be distilled or, if necessary, can be washed using conventional methods to obtain the required purity.

It is seen from the above that a process for recovering components from scrap PET that eliminates the liquid phase crystallization step is accomplished if DMT is crystallized directly from the gas phase reactor product stream without condensation by using temperatures of from about 230° C. to about 290° C. (generally accomplished by heat exchange) and the addition of an inert gas such as nitrogen to the reactor product stream to lower the temperature to 20° C. to 90° C.

The inert gas flow rate and temperature must be set to control the vapor-liquid equilibrium that keeps the more volatile components above their respective dew points to obtain optimum crystal growth and to affect the separation of the more volatile components from the DMT.

While the invention has been described with particular reference to a preferred embodiment, it will be understood by those skilled in the art the various changes can be made and equivalents may be substituted for elements of the preferred embodiment without departing from the scope of the invention. In addition, many modifications may be made to adapt a particular situation in material to a teaching of the invention without departing from the essential teachings of the present invention.

I claim:

1. A process for recovering monomer components from polyethylene terephthalate polyester, the process comprising the steps of:

a) reacting scrap polyethylene terephthalate polyester oligomers melt with alcohol at a temperature at 230° C. to 290° C. by passing excess alcohol vapor through the melt;

b) obtaining the gas phase reactor product of DMT and EG;

c) directly crystallizing DMT from the gas phase reactor by introducing an inert gas to the reactor product stream at a temperature of from 20° C. to 90° C.; and d) collecting the resulting DMT crystals and condensing the ethylene glycol and alcohol vapor in a separate condenser.

2. The process of claim 1 wherein the alcohol is methanol.

3. The process of claim 1 wherein the temperature of the inert gas stream is 85° C.

4. The process of claim 1 wherein the inert gas is nitrogen.

5. The process of claim 1 wherein step a) is carried out from substantially atmospheric pressure to 50 psi.

6. The process of claim 1 wherein the oligomer melt and alcohol reactor temperature is 270° C.

* * * * *